United States Patent [19]
Pinza et al.

[11] Patent Number: 4,719,222
[45] Date of Patent: Jan. 12, 1988

[54] PHARMACOLOGICALLY ACTIVE 5-OXO-1-IMIDAZOLIDINE ACETAMIDE COMPOUNDS

[75] Inventors: Mario Pinza, Milan; Carlo Farina, Como; Silvano Banfi; Ugo Pfeiffer, both of Milan, all of Italy

[73] Assignee: Societe I.S.F. S.p.A., Milan, Italy

[21] Appl. No.: 876,959

[22] Filed: Jun. 20, 1986

[30] Foreign Application Priority Data

Jun. 21, 1985 [IT] Italy ................. 21235 A/85

[51] Int. Cl.$^4$ .................. C07D 233/36; A61K 31/415
[52] U.S. Cl. .................................... 514/385; 514/387; 548/301; 548/302
[58] Field of Search ................. 548/301, 302; 514/385, 514/387

[56] References Cited

U.S. PATENT DOCUMENTS 3,428,646  2/1969  Hellerbach ........................ 548/301

OTHER PUBLICATIONS

Klixkull et al, *Int'l. J. of Pharm.*, 20, 273–284 (1984).
*Chem. Abstract*, 94, 128194u (1981).
*Chem. Abstract*, 63, 2978h (1965).
Hardy et al, *J. Chem. Soc.* Perkin I, 1954–1960 (1977).
Ariyoshi et al, *Bull. Chem. Soc. Japan*, 45, 2015–2018 (1972).
Panetta et al, *J. Org. Chem.*, 37, 302–304 (1972).
Cardinaux et al, *Helv. Chim. Acta.*, 56, 339–347 (1973).

*Primary Examiner*—Henry R. Jiles
*Assistant Examiner*—Bernard I. Dentz
*Attorney, Agent, or Firm*—Nancy S. Mayer; Stuart R. Suter; Alan D. Lourie

[57] ABSTRACT

The invention relates to 5-oxo-1-imidazolidineacetamide derivatives which help restore learning and memory difficulties associated with ageing. A compound of the invention is 2,2-dimethyl-5-oxo-1-imidazolidineacetamide.

13 Claims, No Drawings

PHARMACOLOGICALLY ACTIVE 5-OXO-1-IMIDAZOLIDINE ACETAMIDE COMPOUNDS

This invention relates to new chemical compounds which have useful pharmacological activity, to processes and intermediates for making them, and pharmaceutical compositions containing them.

According to the invention we provide 5-oxo-1imidazolidineacetamide derivatives of Structure (1)

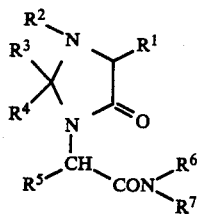

in which
$R^1$ is H, $C_{1-5}$ alkyl (straight or branched), or a phenyl or benzyl group optionally substituted by $C_{1-5}$ alkyl (straight or branched), $C_{1-4}$ alkoxy (straight or branched) or hydroxy;
$R^2$ is H, OH, $C_{1-5}$ alkyl (straight or branched), aryl or acyl;
$R^3$ is H, $C_{1-5}$ alkyl (straight or branched) or phenyl and $R^4$ is $C_{1-5}$ alkyl (straight or branched) or phenyl, or $R^3$ and $R^4$ can together form a 1,4-butylene or 1,5-pentylene group;
$R^5$ is H or $C_{1-5}$ alkyl (straight or branched);
$R^6$ is H, $C_{1-5}$ alkyl (straight or branched), —$CHR^8CONH_2$ or —$CHR^8CONHCHR^9CONH_2$; where $R^8$ and $R^9$ (which can be the same or different) are H or $C_{1-5}$ alkyl (straight or branched); and
$R^7$ is H or $C_{1-5}$ alkyl (straight or branched),
and pharmaceutically acceptable salts thereof.

Preferably $R^1$ is H, methyl or isobutyl, particularly H.
Preferably $R^2$ is H, formyl or acetyl.
Examples of aryl groups are phenyl, and naphthyl which may be optionally substituted by $C_{1-5}$ alkyl (straight or branched), $C_{1-4}$ alkoxy (straight or branched) or hydroxy. Preferably the aryl groups are phenyl, 4-hydroxyphenyl, and 4-methoxyphenyl. Examples of acyl groups are $C_{1-5}$ (straight or branched) alkanoyl groups, particularly formyl, acetyl and propionyl, and aroyl groups, particularly benzoyl and substituted benzoyl groups such as 4-methoxybenzoyl.

Preferably $R^3$ and $R^4$ are both methyl or together form a 1,4-butylene or 1,5-pentylene group, or $R^4$ is methyl or isopropyl and $R^3$ is hydrogen.
Preferably $R^5$ is H, methyl, isopropyl, 1-methylpropyl or isobutyl.
Preferably $R^6$ is H, —$CHR^8CONH_2$ or —$CHR^8CONHCHR^9CONH_2$.
Preferably $R^7$ is H.
Preferably $R^8$ is H, methyl, isopropyl, 1-methylpropyl or isobutyl.
Preferably $R^9$ is H, methyl, isopropyl, 1-methylpropyl or isobutyl.

It will be appreciated that there will be chiral centres present if $R^1$ is other than hydrogen, if $R^3$ and $R^4$ are different, and if any of $R^5$, $R^8$ and $R^9$ are other than hydrogen. The present invention includes all optical isomers of the compounds of Structure (1) in their resolved and partially resolved forms and in the forms of racemic mixtures. When the synthetic precursor for the substituent can be a natural amino acid then preferably that substituent will have the natural (L) configuration.

Particularly preferred compounds of Structure (1) are:
2,2-dimethyl-5-oxo-1-imidazolidineacetamide,
2-(1-methylethyl)-5-oxo-1-imidazolidineacetamide,
2-(2,2-dimethyl-5-oxo-1-imidazolidineacetamido)acetamide,
2-[2-(2,2-dimethyl-5-oxo-1-imidazolidineacetamido)acetamido]acetamide,
2,2,4-trimethyl-5-oxo-1-imidazolidineacetamide,
3-acetyl-2,2-dimethyl-5-oxo-1-imidazolidineacetamide,
3-formyl-2,2-dimethyl-5-oxo-1-imidazolidineacetamide,
(S)-2-[2,2-dimethyl-4-isobutyl-5-oxo-1-imidazolidine acetamido]acetamide,
2-methyl-5-oxo-1-imidazolidineacetamide,
2-(2-isopropyl-5-oxo-1-imidazolidineacetamido)acetamide, and
2-[4S-isobutyl-2-isopropyl-5-oxo-1-imidazolidineacetamido]acetamide,
and their pharmaceutically acceptable salts.

The compounds of Structure (1) can be prepared by reacting a compound of Structure (2)

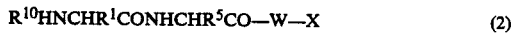

in which $R^{10}$ is H, OH, $C_{1-5}$ alkyl (straight or branched) or aryl, W is a bond, —$NHCHR^8CO$— or —$NHCHR^8CONHCHR^9CO$—, and X is —$NR^6R^7$ or —OH where $R^6$, $R^7$, $R^8$ and $R^9$ are as defined above provided that $R^6$ and $R^7$ are both hydrogen when W is other than a bond, with a carbonyl compound $R^3COR^4$, and when X is —OH the product is converted into the corresponding compound in which X is $NR^6R^7$, and when X is —OH and W is a bond or —$NHCHR^8CO$— the product is converted into a compound in which W is —$NHCHR^8CO$— or —$NHCHR^8CONHCHR^9CO$— and X is —$NR^6R^7$, and when $R^2$ in the product is hydrogen optionally the product is converted into a compound in which $R^2$ is acyl, and optionally the compound of Structure (1) is converted into a pharmaceutically acceptable salt.

When $R^3$ is H the carbonyl compound is an aldehyde and from equimolar to two molar equivalents of the aldehyde are used. When $R^3$ is other than H the carbonyl compound is a ketone and preferably a larger excess of the ketone is used, together with higher temperatures and/or longer reaction times than for the corresponding reactions with aldehydes.

Conversion of a compound in which X is —OH into a compound in which X is —$NR^6R^7$ requires the activation of the carboxyl group or the use of a peptide coupling reagent. This procedure will necessitate the temporary protection of the secondary amino groups in compounds in which $R^2$ is H. Suitable methods for activating carboxyl groups, suitable peptide coupling reagents and protecting groups are all well known to the art and are described for example in 'Peptide Synthesis' by M. Bodansky, Y Klausner and M. Ondetti (Wiley, 1976) and in 'Protective Groups in Organic Synthesis' by T. W. Greene (Wiley, 1981). Examples of activated derivatives of carboxyl groups are acyl chlorides, acyl azides, mixed anhydrides (e.g. formed with an alkyl chloroformate or pivaloyl chloride) and activated esters (e.g. trichlorophenyl, N-hydroxysuccinimido and 1-hydroxybenzotriazole esters). Examples of peptide coupling reagents are carbodiimides and Woodward's Reagent K (N-ethyl-5-phenylisoxazolium-3'-sulphonate). Examples of nitrogen-protecting groups are benzyloxycarbonyl and t-butyloxycarbonyl.

When the peptide side chain contains chiral centres (i.e. when $R^5$, $R^8$ and $R^9$ are other than hydrogen) then the route of synthesis and the reagents will be chosen to ensure that only a small degree of racemisation occurs under the reaction conditions. When racemisation is not a problem and $R^6$ is a monopeptide or dipeptide unit the preferred synthesis is that in which W is a bond and the monopeptide or dipeptide unit is incorporated at a later stage.

The compounds of Structure (1) have useful nootropic activity, that is they help restore learning and memory difficulties associated with ageing and various pathologies including Alzheimer's disease. The present invention therefore provides, in a further aspect a method of restoring learning and treating memory difficulties which comprises administering to a mammal in need thereof a non-toxic effective amount of a compound of Structure (1). To evaluate the nootropic activity, the compounds were submitted to pharmacological tests designed to detect a positive action on cognitive processes disrupted by an experimental cerebral impairment.

In particular the protection against the amnesia induced by maximal electroconvulsive shock (ECS) was studied. The experimental procedure described by Banfi et al., J. Pharmacol. Methods, 8; 255–264 (1982) was followed: Male albino CD Swiss mice from Charles River (Calco, Italy) are used. Mice were 35 days old. The apparatus is essentially the same as described by Essman [Pharm. Res. Commun., 5, 295–302, (1973)]. The passage from a light box ($10 \times 10 \times 12$ cm) into a dark one ($23 \times 16 \times 12$ cm) was punished by unavoidable foot shocks (0.3 mA, 50 Hz, 5 sec). In order to erase newly encoded information in the memory, a maximal ECS (30 mA, 150 msec, 50 Hz) is given to the mice by corneal electrodes immediately after the trial. The re-test is performed 24 hr after ECS. Mice that did not cross from the light box into the dark one in 60 sec were considered as not affected by the retrograde amnesic effect of ECS. Groups of control animals were submitted to sham ECS to demonstrate the amnesic action of ECS. Saline or tested compounds are injected i.p. to groups of at least 20 mice 1 hr before the conditioning trial. The number of animals showing retention over the total number in each treated group is compared with that of controls by the chi square test.

The compounds under study are tested at the doses of 0.3 mg/kg, 1 mg/kg, 10 mg/kg and 30 mg/kg. The difference in percentage retention between the control saline-treated mice submitted to ECS and those submitted to sham ECS demonstrated the amnesic action of ECS. The degree of protective activity of the compounds is evaluated by comparing the groups treated with the compounds plus ECS to the group treated with saline alone plus ECS. Significant protective action was observed, for example, after intraperitoneal administration of 2-(1-methylethyl)-5-oxo-1-imidazolidineacetamide or 2-(2,2-dimethyl-5-oxo-1-imidazolidineacetamido)acetamide in a dose range from 0.3 to 30 mg/kg.

The specific mechanism of action of the compounds can be characterised by high affinity choline uptake determinations using synaptosomal preparations from cortical and hippocampal rat tissues, for example as described by F. Pedata et al., Clinical Neuropharmacology, 7, (Suppl. 1), 772–3, (1984). Activity in this test indicates that the compounds might enhance cholinergic neurotransmission by increasing the amount of choline pre-synaptically available which in turn would lead to an increase in brain acetylcholine levels, thus improving the performance of brains in which choline and acetylcholine levels were abnormally low.

An alternative method for investigating the selective action of the compounds of Structure (1) is to test their activity in rats against both the disruptive action of scopolamine on mnestic trace and on the reduction of acetylcholine levels in hippocampus.

In order to use a compound of Structure (1) for the therapeutic treatment of humans and animals, it is normally formulated in accordance with standard pharmaceutical practice as a pharmaceutical composition. Therefore in another aspect the present invention provides a pharmaceutical composition which comprises a compound of Structure (1) and a pharmaceutically acceptable carrier.

The compounds of the Structure (1) may be administered in standard manner for the treatment of the indicated diseases, for example orally, parenterally, rectally, transdermally or via trans-mucosal (for example sub-lingual, or buccal or insufflatory) administration.

The compounds of the Structure (1) which are active when given orally or via sub-lingual or buccal administration can be formulated as syrups, tablets, capsules and lozenges. A syrup formulation will generally consist of a suspension or solution of the compound or salt in a liquid carrier for example, ethanol, glycerine or water with a flavouring or colouring agent. Where the composition is in the form of a tablet, any pharmaceutical carrier routinely used for preparing solid formulations may be used. Examples of such carriers include magnesium stearate, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be utilised, for example aqueous gums, celluloses, silicates or oils and are incorporated in a soft gelatin capsule shell.

Typical parenteral compositions consist of a solution or suspension of the compound of the Structure (1) in a sterile aqueous or non-aqueous carrier optionally containing a parenterally acceptable oil, for example polyethylene glycol, polyvinylpyrrolidone, lecithin, arachis oil, or sesame oil.

A typical suppository formulation comprises a compound of Structure (1) which is active when administered in this way, with a binding and/or lubricating agent, for example polymeric glycols, gelatins, cocoa-butter or other low melting vegetable waxes or fats.

Typical transdermal formulations comprise a conventional aqueous or non-aqueous vehicle, for example a cream, ointment, lotion or paste or can be in the form of a medicated plaster, patch or membrane.

Preferably the composition is in unit dosage form, for example a tablet or capsule, so that the patient may administer to himself a single dose.

Piracetam is a compound which is used in the treatment of senile dementia and related disease conditions. The compounds of Structure (1) can be administered in similar regimes to those established for piracetam with any appropriate adjustment in dose levels or frequency of dosing having regard to the greater activity and better pharmacological profile of the compounds of Structure (1).

Each dosage unit for oral administration contains suitably from 0.5 mg/Kg to 50 mg/Kg, and preferably from 1 mg/Kg to 8 mg/Kg, and each dosage unit for parenteral administration contains suitably from 0.1 mg/Kg to 10 mg/Kg, of a compound of Structure (1).

The daily dosage regimen for oral administration is suitably about 0.5 mg/Kg to 100 mg/Kg, more suitably about 1 mg/Kg to 25 mg/Kg of a compound of Structure (1) calculated as the free base. The active ingredient may be administered from 1 to 6 times daily. The compounds of Structure (1) may be co-administered with other pharmaceutically active compounds, for example in combination, concurrently or sequentially, particularly with other compounds used in the treatment of elderly patients e.g. tranquillisers, diuretics antihypertensives, vasodilator and inotropic agents.

The invention is illustrated by the following Examples.

EXAMPLE 1

2,2-Dimethyl-5-oxo-1-imidazolidineacetamide

A. (1) To an ice cold solution of thionyl chloride (5 ml) in dry ethanol (50 ml) a solution of sodium 2,2-dimethyl-5-oxo-1-imidazolidineacetate (4 g) in dry ethanol (50 ml) was added dropwise. The mixture was stirred at 0° C. for 1 hour, then at room temperature overnight. After evaporation under reduced pressure, the residue was taken up with a saturated solution of sodium hydrogen carbonate and extracted with 3×100 ml of dichloromethane. The organic layer was dried and evaporated, to yield ethyl 2,2-dimethyl-5-oxo-1-imidazolidineacetate (2.57 g) as a colorless oil (Rf. 0.49, methanol/acetone 1:1; silica gel plates). Oxalate salt m.p. 109°–113° C. (ethanol/diethyl ether).

(2) An ice cold solution of ethyl 2,2-dimethyl-5-oxo-1-imidazolidineacetate (2 g) in methanol (150 ml) was saturated with gaseous ammonia. The solution was stirred at room temperature for 36 hours. After evaporation the residue was chromatographed on a silica gel column, eluting with dichloromethane/methanol 6:4. The selected fractions were collected, evaporated and the residue was crystallized from ethanol, to give 1 g of the title compound, as a white powder, m.p. 144°–146° C.

(B) To a solution of glycylglycinamide acetate (10 g) in methanol (250 ml) and acetone (125 ml), was added Amberlite IRA-68 resin (20 g) (available from Rohm & Haas, Philadelphia, USA). Amberlite is a registered trade mark and IRA-68 is a weakly basic resin. The suspension was stirred at room temperature for 1 hour, then resin was filtered off and the solution was evaporated under reduced pressure. The residue was suspended in refluxing acetone (250 ml) and methanol was added to obtain a clear solution, which was refluxed for 2 hours. Evaporation and trituration of the residue with acetone gave 6.85 g of the title compound.

EXAMPLE 2

(1) To 50 ml of anhydrous ethanol stirred at 0°–5° C., 2 ml thionyl chloride were added. At the same temperature 2.1 g (0.01 mol) of sodium 2-(1-methylethyl)-5-oxo-1imidazolidineacetate were added. The suspension obtained was stirred at 0° C. for 1 hour and at room temperature for 2 hours. The solvent was evaporated under reduced pressure and the residue taken up with ethyl acetate. The solid residue was filtered off and the solvent evaporated. The residue was dissolved in a saturated solution of sodium hydrogen carbonate and extracted with 3×50 ml of dichloromethane. The organic layers were dried and evaporated to give ethyl 2-(1-methylethyl)-5-oxo-1imidazolidineacetate (0.9 g) as a pale-yellow oil (42%) (Rf 0.6, ethyl acetate/dichloromethane 6:4; silica gel plates). Hydrochloride salt, m.p. 148°–149° C. (methanol/ethyl acetate).

(2) An ice cold solution of 3.8 g (0.018 mol) of ethyl 2-(1-methylethyl)-5-oxo-1-imidazolidineacetate in 100 ml of methanol was saturated with gaseous ammonia. The solution was stirred at room temperature overnight and the solvent was evaporated under reduced pressure, to give 2-(1-methylethyl)-5-oxo-1-imidazolidineacetamide (3.4 g) as a viscous oil (Rf 0.33; ethyl acetate/methanol 6:4; silica gel plates). Monohydrate of sulphate salt m.p. 64° C. resolidifying with final decomposition at 114°–118° C.

EXAMPLE 3

2-(2,2-Dimethyl-5-oxo-1-imidazolidineacetamido)acetamide

To a solution of glycylglycylglycinamide acetate (800 mg) in methanol (8 ml) and acetone (15 ml), Amberlite IRA-68 resin (2 ml) was added. The suspension was stirred at room temperature for 1 hour, then the resin was filtered off and the solution was evaporated under reduced pressure. The residue was suspended in acetone and stirred at room temperature overnight. The precipitate was collected and crystallized from ethyl acetate, to give the title compound, as a white powder, m.p. 102°–105° C. dec.

EXAMPLE 4

2-[2-(2,2-Dimethyl-5-oxo-1-imidazolidineacetamido) acetamido]acetamide

The same procedure of the Example 3 starting from triglycylglycinamide acetate afforded the title compound as a white powder, Rf 0.2 (dichloromethane/methanol 1:1; silica gel plates), m.p. 100°–105° dec.

EXAMPLE 5

2,2,4-Trimethyl-5-oxo-1-imidazolidineacetamide

The same procedure of the Example 3 starting from alanylglycinamide acetate afforded the title compound as a white hygroscopic solid, Rf 0.48 (dichloromethane/methanol 1:1; silica gel plates). Maleate salt, m.p. 142°–144° C. dec.

EXAMPLE 6

3-Acetyl-2,2-dimethyl-5-oxo-1-imidazolidineacetamide

A solution of 2,2 dimethyl-5-oxo-1-imidazolidineacetamide (1.7 g) in acetic anhydride (9 ml) was stirred at 70°–80° C. for 5 minutes. The precipitate was collected and washed with acetone, affording the title compound as a white powder, m.p. 188°–189° C. (ethyl acetate).

EXAMPLE 7

3-Formyl-2,2-dimethyl-5-oxo-1-imidazolidineacetamide

The same procedure of Example 6, using mixed acetic-formic anhydride yielded the title compound as a white powder m.p. 211°–213°.

EXAMPLE 8

(S)-2-[2,2-Dimethyl-4-isobutyl-5-oxo-1-imidazolidine acetamido]acetamide

The same procedure of Example 3 starting from L-leucylglycylglycinamide hydrochloride, afforded the title compound as a white hygroscopic solid (Rf 0.47 dichloromethane-methanol 7:3, silica gel plates).

EXAMPLE 9

2-Methyl-5-oxo-1-imidazolidineacetamide

A solution of glycylglycinamide (0.5 g) and acetaldehyde (0.4 ml) in methanol (5 ml) was stirred at room temperature for 8 hours. Evaporation of the solvent gave a residue which was chromatographed on a silica gel column (eluant dichloromethane/methanol 75:25). The selected fractions were collected, evaporated to give the title compound (Rf=0.3, dichloromethane/methanol 7:3, silica gel plates). Mass spectrum (E.I., 70 eV, 1.5 mA), m/z=142 (M+ −CH$_3$), 99.

EXAMPLE 10

2-(2-Isopropyl-5-oxo-1-imidazolidineacetamido)acetamide

The same procedure of example 9, starting from glycylglycylglycinamide and isobutyraldehyde, afforded the title compound as a white hygroscopic solid, m.p. 65°-70° C. Mass spectrum (E.I., 70 eV, 1.5 mA), m/z=199 (M+ −C$_3$H$_7$).

EXAMPLE 11

2-[4S-Isobutyl-2-isopropyl-5-oxo-1-imidazolidineacetamido]acetamide

The same procedure of example 9, starting from L-leucylglycylglycinamide and isobutyraldehyde, afforded the title compound as a diastereoisomeric mixture, Rf 0.58 (dichloromethane-methanol 7:3) Mass spectrum (E.I., 70 eV, 1.5 mA), m/z=255 (M+ −C$_3$H$_7$).

EXAMPLE 12

| Composition for 1 tablet | |
|---|---|
| 2-(1-methylethyl)-5-oxo-1-imidazolidine-acetamide | 100 mg |
| lactose | 100 mg |
| corn starch | 80 mg |
| talcum | 11.5 mg |
| silicon dioxide | 4 mg |
| magnesium stearate | 2.5 mg |
| gelatine | 2.0 mg |

For the manufacture of 1000 tablets, 100 g of active ingredient are mixed with 100 g of lactose and 70 g of corn starch. The mixture is moistened with an aqueous solution of gelatine and then granulated and dried. The granules are mixed with 10 g of corn starch, 11.5 g of talcum, 4.0 g of silicon dioxide and 2.5 g of magnesium stearate and the mixture is pressed into tablets each weighing 300 mg and having the active ingredient content of 100 mg. The tablets can have different shapes and breaking notches for finer adjustment of the dosage.

What is claimed is:

1. A compound of Structure (1)

$$
\begin{array}{c}
R^2 \\
R^3 \diagdown N \diagup R^1 \\
R^4 \diagup \diagdown \diagup \\
N = O \\
R^5 \diagdown CH \diagdown CON \diagup R^6 \\
\phantom{R^5} \phantom{CON} R^7
\end{array}
\quad (1)
$$

wherein
R$^1$ is H, C$_{1-5}$ alkyl (straight or branched), or a phenyl or benzyl group optionally substituted by C$_{1-5}$ alkyl (straight or branched), C$_{1-4}$ alkoxy (straight or branched) or hydroxy;

R$^2$ is H, OH, C$_{1-5}$ alkyl (straight or branched), phenyl or naphthyl optionally substituted by C$_{1-5}$ alkyl (straight or branched), C$_{1-4}$ alkoxy (straight or branched), or hydroxy or C$_{1-5}$ alkanoyl (straight or branched), benzoyl, or 4-methoxybenzoyl;

R$^3$ is H, C$_{1-5}$ alkyl (straight or branched) or phenyl and R$^4$ is C$_{1-5}$ alkyl (straight or branched) or phenyl, or R$^3$ and R$^4$ can together form a 1,4-butylene or 1,5-pentylene group, with the proviso that when R$^3$ is H, R$^4$ is C$_{2-5}$ alkyl (straight or branched);

R$^5$ is H or C$_{1-5}$ alkyl (straight or branched);

R$^6$ is H, C$_{1-5}$ alkyl (straight or branched), —CHR$^8$CONH$_2$ or —CHR$^8$CONHCHR$^9$CONH$_2$; where R$^8$ and R$^9$ (which can be the same or different) are H or C$_{1-5}$ alkyl (straight or branched); and R$^7$ is H or C$_{1-5}$ alkyl (straight or branched), or a pharmaceutically acceptable salt thereof.

2. A compound according to claim 1 in which R$^1$ is is selected from the group consisting of H, methyl and isobutyl.

3. A compound according to claim 1 in which R$^2$ is selected from the group consisting of H, formyl and acetyl.

4. A compound according to any one of claims 1 to 3 in which R$^3$ and R$^4$ are both methyl or together form a 1,4-butylene or 1,5-pentylene group, or R$^3$ is hydrogen and R$^4$ is isopropyl, 5. A compound according to claim 4 in which R$^5$ is selected from the group consisting of H, methyl, isopropyl, 1-methylpropyl and isobutyl.

6. A compound according to claim 5 in which R$^6$ is selected from the group consisting of H, —CHR$^8$CONH$_2$ and —CHR$^8$CONHCHR$^9$CONH$_2$.

7. A compound according to claim 6 in which R$^7$ is H.

8. A compound according to claim 7 in which R$^8$ is selected from the group consisting of H, methyl, isopropyl, 1-methylpropyl and isobutyl.

9. A compound according to claim 8 in which R$^9$ is selected from the group consisting of H, methyl, isopropyl, 1-methylpropyl and isobutyl.

10. A compound according to claim 1 which is 2-(1-methylethyl)-5-oxo-1-imidazolidineacetamide, or 2-(2,2-dimethyl-5-oxo-1-imidazolidineacetamido)acetamide.

11. A compound according to claim 1 selected from the group consisting of:
2,2-dimethyl-5-oxo-1-imidazolidineacetamide,
2-[2-(2,2-dimethyl-5-oxo-1-imidazolidineacetamido)acetamido]acetamide,
2,2,4-trimethyl-5-oxo-1-imidazolidineacetamide,
3-acetyl-2,2-dimethyl-5-oxo-1-imidazolidineacetamide, 3-formyl-2,2-dimethyl-5-oxo-1-imidazolidineacetamide,
(S)-2-[2,2-dimethyl-4-isobutyl-5-oxo-1-imidazolidine acetamido]acetamide,
2-(2-isopropyl-5-oxo-1-imidazolidineacetamido)acetamide, and
2-[4S-isobutyl-2-isopropyl-5-oxo-1-imidazolidineacetamido]acetamide.

12. A pharmaceutical composition useful in restoring learning and treating memory difficulties comprising an effective amount of a compound according to any one of claims 1 to 11 and a pharmaceutical carrier.

13. A method of restoring learning and treating memory difficulties which comprises administering to a mammal in need thereof a non-toxic effective amount of a compound of structure (1) or a pharmaceutically acceptable salt thereof.

* * * * *